United States Patent
Takeuchi

[19]

[11] Patent Number: 6,155,268
[45] Date of Patent: Dec. 5, 2000

[54] FLAVOR-GENERATING DEVICE

[75] Inventor: Manabu Takeuchi, Tokyo, Japan

[73] Assignee: Japan Tobacco Inc., Tokyo, Japan

[21] Appl. No.: 09/120,457

[22] Filed: Jul. 23, 1998

[30] Foreign Application Priority Data

Jul. 23, 1997 [JP] Japan ................................. 9-197033

[51] Int. Cl.⁷ ............................................. A24F 47/00
[52] U.S. Cl. ........................................... 131/273; 131/194
[58] Field of Search ................................. 131/335, 271,
131/273, 194, 336, 272

[56] References Cited

U.S. PATENT DOCUMENTS

| | | |
|---|---|---|
| 4,288,396 | 9/1981 | Ottestad . |
| 4,303,083 | 12/1981 | Burruss, Jr. . |
| 4,805,614 | 2/1989 | Lerner . |
| 4,945,931 | 8/1990 | Gori . |
| 5,060,671 | 10/1991 | Counts et al. . |
| 5,144,962 | 9/1992 | Counts et al. . |
| 5,269,327 | 12/1993 | Counts et al. . |
| 5,666,977 | 9/1997 | Higgins et al. .................. 131/194 |
| 5,743,251 | 4/1998 | Howell et al. . |

FOREIGN PATENT DOCUMENTS

| | | |
|---|---|---|
| 0295122A2 | 12/1988 | European Pat. Off. . |
| 0358114A2 | 3/1990 | European Pat. Off. . |
| WO 95/01137A1 | 1/1995 | WIPO . |

*Primary Examiner*—James Derrington
*Assistant Examiner*—Rob McBride
*Attorney, Agent, or Firm*—Birch, Stewart, Kolasch & Birch, LLP

[57] ABSTRACT

A flavor-generating device includes a chamber having an air inlet port and a flavor inhalation port, and defining a gas passageway between the air inlet port and the inhalation port. A liquid container for storing a liquid flavor source is provided, and is maintained at substantially an atmospheric pressure. At least one liquid passageway is provided in fluid communication with the liquid flavor source at its first end portion and with the gas passageway at its second end portion. The liquid passageway transports the liquid flavor source therethrough by capillary force. A heater heats and evaporates the liquid flavor source at the second end portion of the liquid passageway.

18 Claims, 8 Drawing Sheets

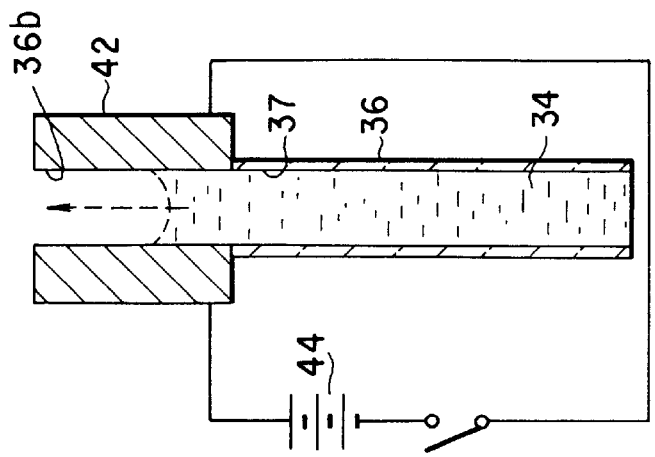
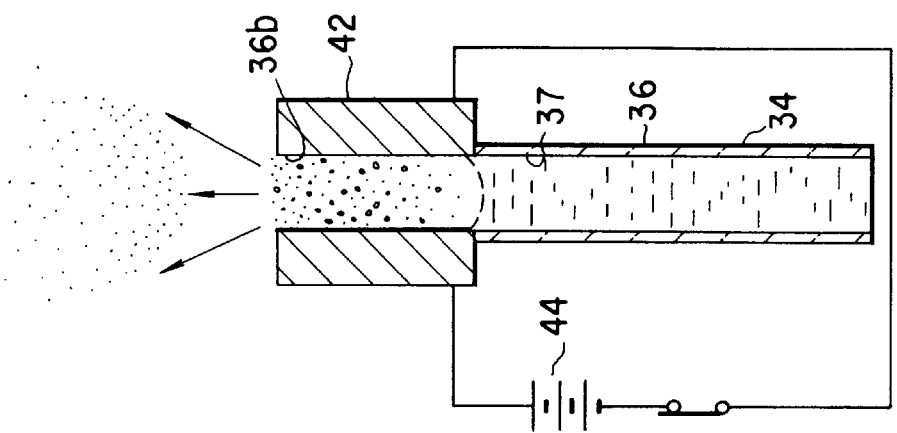
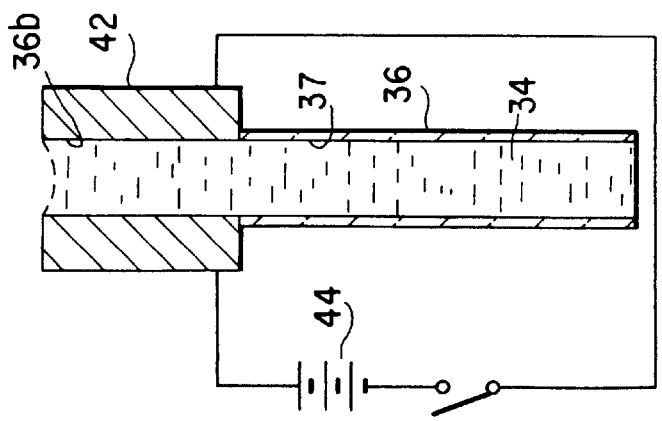

FLAVOR-GENERATING DEVICE

BACKGROUND OF THE INVENTION

The present invention relates to a flavor-generating device for enjoying inhalation of flavor or for enjoying simulated smoking, and more particularly, to a flavor-generating device for generating flavor which is to be inhaled by a user by heating a liquid. flavor source without relying on combustion.

Various types of flavor-generating devices in which a flavor material is evaporated by heating for enjoying inhalation of flavor have been proposed to date.

For example, Japanese Patent Disclosure (Kokai) No. 3-232481 discloses a typical concept of a conventional simulated smoking article. In this flavor-generating device, a rod-like solid flavor material is used, and the flavor or inhalation target is generated by heating the solid flavor material with a heating element. In a flavor-generating device of this type, a large amount of solid flavor material is wasted where the flavor material is kept continuously heated. Disadvantageously, where the solid flavor generation material is heated when a user wishes to inhale the flavor generated from the flavor material, a large time lag is generated between the actual inhalation of the flavor by the user and the generation of the flavor.

A flavor-generating device capable of coping with the above-noted difficulty is disclosed in, for example, Japanese Patent Disclosure No. 3-277265. The disclosed device has a solid flavor material divided into a number of portions, wherein the divided portions of the solid flavor material are heated one by one every time a user takes one puff of the flavor so as to generate the flavor which is to be inhaled by the user. In this flavor-generating device, the solid flavor material and the heating element collectively constitute an integral flavor-generating means. It follows that, after consumption of the flavor material, it is necessary to replace or discard the heating element together with the flavor material. This may be expensive and give rise to an environment problem.

U.S. Pat. No. 4,945,931 discloses a simulated smoking article using a pressurized aerosol container. In this device, vanes are rocked in response to the inhaling action of a user so as to mechanically open the outlet port of the aerosol container and, thus, to release the aerosol. This prior art also discloses a modification in which a heating element for warming the aerosol cooled by the heat of evaporation is mounted at the outlet port of the aerosol container. In each of these devices, however, a pressurized aerosol is confined in the container by a valve which is opened or closed in response to the inhaling action of the user. It follows that a large amount of the aerosol may be leaked to the outside once the valve is opened. In other words, in each of these prior art articles, it is impossible to release continuously a predetermined suitable amount of the aerosol every time a user takes a single puff. Rather, all the pressurized aerosol tends to be released in two or three inhaling actions of the user.

BRIEF SUMMARY OF THE INVENTION

Accordingly, it is an object of the present invention to provide a flavor-generating device which can be driven with a low energy, which effectively prevents a flavor source from being wasted, and which permits generating flavor when a user takes a puff of the flavor, substantially without a time lag.

Another object of the invention is to provide a flavor-generating device which can be made small in size and light in weight.

According to the present invention, there is provided a flavor-generating device comprising a chamber having an air inlet port for introducing the air thereinto and an inhalation port through which a user inhales a flavor, and defining a gas passageway between the air inlet port and the inhalation port; a liquid container for storing a liquid containing a flavor substance, and maintained at substantially an atmospheric pressure; at least one liquid passageway having a first end portion which is in a fluid communication with the liquid and a second end portion which is in a fluid communication with the gas passageway, for transporting the liquid from the liquid container to the second end portion by capillary force; and a heater mounted at the second end portion of the liquid passageway, for heating and gasifying or evaporating the liquid transported from the liquid container.

In the flavor-generating device of the present invention, a liquid containing a flavor substance, i.e., a liquid flavor source, is transported from within a liquid container through the liquid passageway by a capillary force exerted by the liquid passageway. Thus, if the preceding liquid flavor source is gasified or evaporated at the outlet end portion of the liquid passageway, the succeeding liquid flavor source is supplied to the outlet end portion of the liquid passageway by the capillary force. It follows that the flavor-generating device of the present invention can be driven as a whole at a low energy. As a result, it is possible to suppress waste of the flavor source. In addition, the flavor can be generated when the user takes a puff of the flavor. It should be noted in particular that the heater can be controlled on the basis of a signal from a sensor for detecting the inhaling action of the user, with the result that the flavor can be supplied to the user with a high stability.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 2A to 2C illustrate the operation of the flavor-generating device shown in FIG. 1;

DETAILED DESCRIPTION OF THE INVENTION

Figure 1:
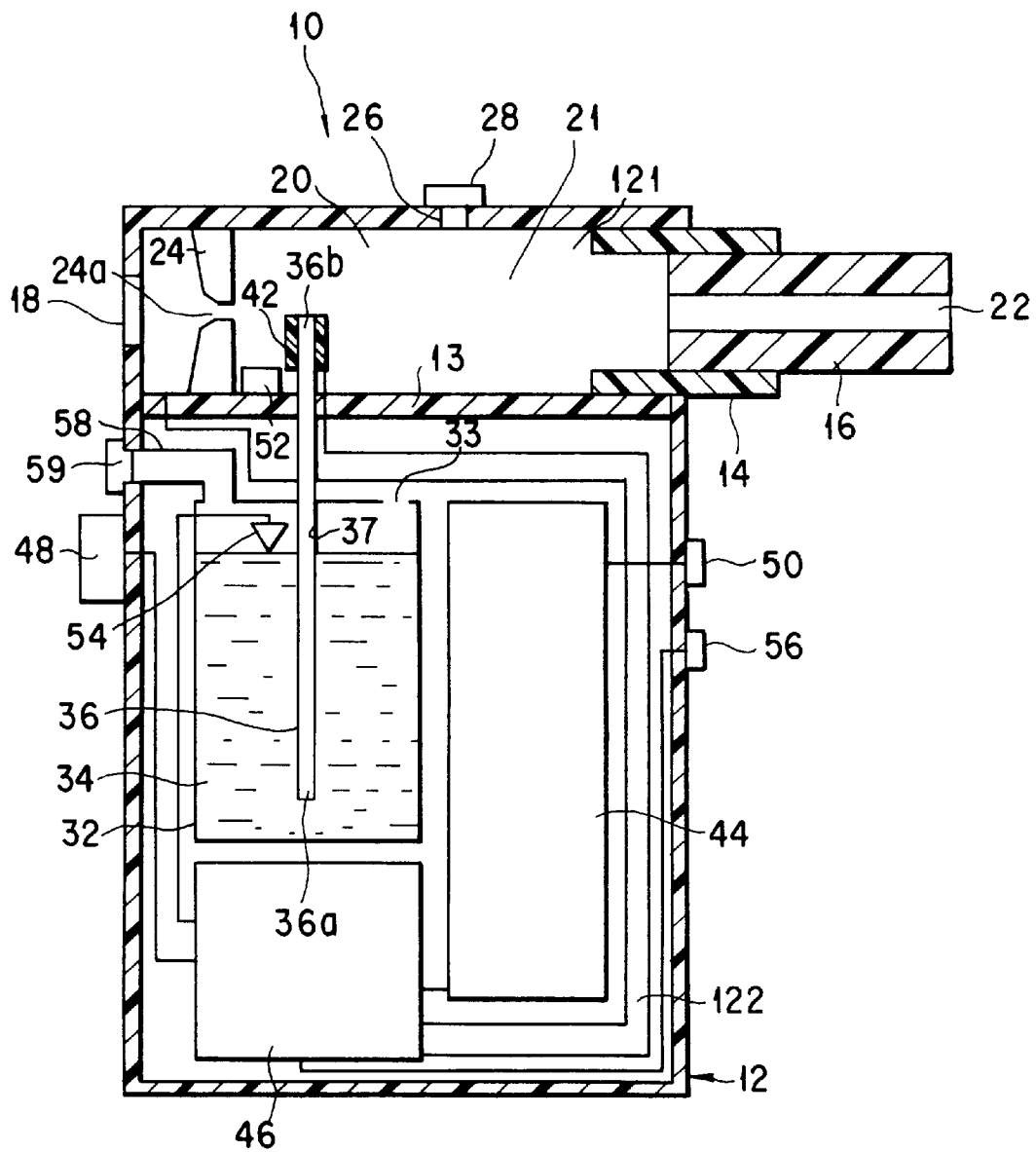
FIG. 1 is a sectional view of a flavor-generating device according to one embodiment of the present invention.

One feature of the present invention resides in that the transportation of a liquid flavor source from the liquid container containing the same to the heater site is effected by the capillary force or capillarity.

In the present invention, the liquid passageway through which the liquid flavor source is transported by the capillary force can be constituted by the inner region of at least one capillary tube, a gap or space between at least two plates spaced apart from each other in substantially parallel, or an inter-communicating void or pore structure filled in an enclosure. The intercommunicating pore structure refers to a structure having intercommunicating voids or pores through which the liquid may be elevated from the inlet of the passageway which is in fluid communication with the liquid flavor source contained in the liquid container to the outlet of the passageway by the capillary force. Representative examples of the structure include open-cell foamed structure, and bundled fibers, but should not be limited thereto.

The height from the liquid level of the liquid flavor source to the outlet of the liquid passageway is a height or vertical distance within which the liquid flavor source may be elevated by the capillary force, and is determined by the properties of the liquid flavor source and the width of the liquid passageway (the diameter for the capillary tube, the gap distance for the substantially parallel plates, etc.). When the passageway is inclined, the height is not the length of the liquid passageway, but the vertical distance from the liquid level of the liquid flavor source to the outlet of the liquid passageway.

The height h can be calculated from the following equation:

$$h = 2\upsilon \cos \theta / d\rho g \quad (1)$$

where $\upsilon$ is the surface tension of the liquid flavor source, $\theta$ is the contact angle of the liquid flavor source with the material which constitutes the liquid passageway, d is the width of the liquid passageway, $\rho$ is the density of the liquid flavor source, and g is the gravitational acceleration.

When the liquid passageway is defied by the intercommunicating pore structure as note above, the equation (1) is not directly applied. In such a case, the equation (1) can be applied, using, as d, an average diameter or size of the voids or pores in the intercommunicating pore structure.

Since the liquid level is lowered due to the gasification or evaporation, including the gasification by intentional heating, of the liquid flavor source, it is desirable that the height be determined taking the possible lowest level of the liquid flavor source into account. Further, it is preferred that the inlet of the liquid passageway reach the possible lowest level of the liquid flavor source in the container.

In the present invention, it is preferred that the liquid level of the liquid flavor source be under substantially atmospheric pressure because the liquid flavor source is elevated from the liquid container to the outlet of the liquid passageway by the capillary force as noted above. The inside of the container can be kept under the atmospheric pressure by providing, at the upper part of the container, a through hole, such as a pin hole, which communicates with the atmosphere outside the container.

There will now be described below some of the embodiments of the present invention.

FIG. 1 shows the construction of a flavor-generating device 10 according to one embodiment of the present invention. In the device 10, the liquid passageway is constituted by a capillary tube.

As shown in FIG. 1, the flavor-generating device 10 includes a casing 12 made of plastic, metal, ceramic, wood, etc. The inner space of the casing 12 is partitioned into an upper chamber 121 and a lower chamber 122 by a partition wall 13. As will be described herein later, the upper chamber 121 is used as a gas passageway 20 for forming a gaseous stream of a flavor which is to be inhaled by a user. On the other hand, the lower chamber 122 is used as a housing for housing a liquid container 32, a power source 44 and a control circuit.

An inhalation port holder 14 defining a cylindrical opening is mounted at one side end portion of the upper chamber 121 of the casing 12. A mouth piece 16 having an inhalation port 22 through which a user inhales a flavor is detachably inserted into the holder 14. The mouth piece 16, which is directly taken in the mouth of a user, is made of, for example, a plastic material or wood. Incidentally, it is possible to insert a filter into the holder 14 in place of using the mouth piece 16.

On the other hand, an air intake port 18 for introducing the air into the upper chamber 121 is formed on the other side portion of the upper chamber 121. The gas passageway 20 is defined within the upper chamber 121 of the casing 12, between the air intake port 18 and the inhalation port 22. It is possible to set the air intake port 18 in a manner to have an opening area conforming with a predetermined air intake amount. It is also possible to arrange an adjusting ring (not shown) having a plurality of openings in a manner to surround the air intake port 18 of the casing 12. In this case, the air flow rate into the gas passageway 20 can be adjusted by adjusting the position of the adjusting ring relative to the air intake port 18.

A squeeze plate 24 having a squeeze hole 24a formed in the central portion is arranged within the gas passageway 20 and positioned close to the air intake port 18. The squeeze hole 24a of the squeeze plate 24 act to regulate or direct the air introduced from the intake port 18 selectively toward a outlet portion 36b of a capillary tube 36 described in detail below.

The free space between the outlet portion 36b of the capillary tube 36 and the inhalation port 22 can act as a cooling chamber 21 which constitutes a part of the gas passageway. Corresponding to the cooling chamber 21, an outer air introduction hole 26 is formed through the ceiling of the upper chamber 121 to permit the outer air to be introduced into the cooling chamber 21. A gas containing a flavor, which is formed by the heating of the liquid flavor source with a heater 42, is mixed with the outer air within the cooling chamber 21 so as to be cooled and, then, flows to reach the inhalation port 22. The outer air introduction hole 26 can be set to have an opening area conforming with a predetermined outer air introduction amount. It is also possible to arrange an adjusting shutter 28 having a plurality of openings in the casing 12 in a manner to surround the outer air introduction hole 26, as shown in the drawing. In this case, the amount of the outer air introduced into the cooling chamber 21 can be adjusted by adjusting the position of the adjusting shutter 28 relative to the outer air introduction hole 26.

Further, a filter (not shown) can be arranged between the cooling chamber 21 and the inhalation port 22 in a manner to cover the inhalation port 22. The filter serves to control the pressure loss to permit the gas containing the flavor to be inhaled comfortably by a user. The material of an ordinary tobacco filter such as cellulose acetate or pulp can be used for forming the filter.

On the other hand, the liquid container 32 housing a liquid flavor source 34 is fixed within the lower chamber 122 of the casing 12. The liquid flavor source 34 is housed in the container 32 in an amount conforming with a plurality of puffs of a user. The liquid flavor source 34 contains at least a flavor substance. However, in order to add smoke to the flavor, it is possible for the liquid flavor source 34 to contain a substance forming aerosol when heated. As a substance for forming an aerosol, it is possible to use alcohols, sugars, water and a mixture of at least two of these materials. The alcohols used in the present invention include, for example, glycerin, propylene glycol, and a mixture thereof.

To be more specific, it is possible for the liquid flavor source 34 to contain extracts from various natural products and/or components thereof depending on the use of the flavor-generating device. For example, where the device is used as a simulated smoking article, it is possible for the liquid flavor source 34 to contain tobacco components such as tobacco extracts and a tobacco smoke condensate.

The capillary tube 36 for transporting the liquid flavor source by the capillary force is inserted within the liquid container. The capillary tube 36 defines a liquid passageway 37 for the liquid flavor source, and its lower end 36a is positioned in the vicinity of the bottom of the liquid container 32.

In view of the liquid flavor source 34 mentioned above, preferably the inner diameter of the capillary tube 36 is set to fall within a range of 0.01 mm and 3 mm, more preferably a range of 0.05 mm to 1 mm, and particularly preferably 0.1 mm and 0.8 mm.

In order to ensure the transfer of the liquid flavor source 34 by the capillary force, the liquid container 32 is provided with an opening 33 communicating with the outer atmosphere so as to maintain the inner pressure of the liquid container 32 at an atmospheric pressure. It is desirable for the opening 33 to be formed at the highest position of the container 32 during the ordinary operation of the flavor-generating device and to have a sufficiently small diameter so that the liquid flavor source 34 may not leak to the outside therethrough even if the device is inadvertently turned upside down. For example, a pin hole extending through the wall of the container 32 satisfies the particular requirements of the opening 33.

The upper end portion of the capillary tube 36 protrudes into the upper chamber 121 of the casing 12 somewhat downstream of the squeeze plate 24 and is equipped with the heater 42 serving to gasify the liquid flavor source 34. In the embodiment shown in FIG. 1, the heater 42 consists of a tubular body mounted to the capillary tube 36 and having an inner diameter equal to that of the capillary tube 36. In other words, the outlet port 36a of the liquid passageway 36 is formed by the heater 42 itself. An electric power is supplied from a power source 44 detachably mounted within the lower chamber 122 of the casing 12 to the electric heater 42. It is desirable to use as the power source 44 a DC power source available on the market such as a primary battery (dry battery), or a secondary battery (rechargeable battery). However, it is also possible to use an AC power source as the power source 44. It is also possible to mount the power source 44 outside the casing 12 or to mount the power source 44 separately so as to use an electric wire connecting the power source 44 to the casing 12.

The heater 42 and the power source 44 are driven under the control of the control circuit 46 fixed within the lower chamber 122. To the control circuit 46, a switch 48 for the heater 42 which can independently turn the heater on, and a sensor 52 for detecting the inhalation action of a use are connected. Further, a switch 50 for the on/off operation of the power source 44 is connected to the power source 44.

The switches 48 and 50 are provided on the outer surface of the lower chamber 122 of the casing 12.

When the device is not used, operation of the device can be ceased by turning the power source switch 50 off manually. Of course, when the device is used, firstly the power source switch is turned on. Further, the heater switch 48, when turned on after the power source switch 50 is turned on, can drive the heater 42 independently of the detection, by the sensor 52, of the inhalation action of a user. That is, after the power source 44 is driven, the heater can be made into a heated state by turning on the heater switch 48. When the control circuit 46 detects the on state of the heater switch 48, it ceases the operation of the sensor 52.

Each of the switches 48 and 50 has a mechanism equal to a general small depression type switch such as a micro limit switch having an electrical contact.

The sensor 52 for detecting the inhaling action of the user is arranged within the upper chamber 121 of the casing 12, and is positioned between the squeeze plate 24 and the heater 42. It is possible to use as the sensor 52 a general pressure sensor for detecting a change in the pressure within the chamber 121 as a change in electrical resistance, as a change in electrical capacitance or as a piezoelectric electromotive force, or a rocking vane type sensor for detecting a gas stream within the chamber 121.

The control circuit 46 serves to start up the heater 42 based on the signal from the heater switch 48 or in accordance with the inhaling action of the user based on the signal from the sensor 52 so as to gasify the liquid flavor source 34 at the outlet portion 36b of the capillary tube 36. The signal processing and control are performed within the control circuit 46 in accordance with, for example, a known analog control, a two-position control or a combination thereof.

A liquid amount sensor 54 for detecting the remaining amount of the liquid flavor source 34 is arranged within the liquid container 32. The sensor 54 may consist of a contact type sensor serving to detect a change in the electrical conductivity of the liquid container 32 accompanying a change in the remaining amount of the liquid flavor source 34. Also, an electrical display means, e.g., a lamp 56 which may be constituted by a light emitting diode, is arranged on the outer surface of the lower chamber 122 of the casing 12 in order to inform the user that the remaining amount of the liquid flavor source 34 within the liquid container 32 is small. Each of the liquid amount sensor 54 and the lamp 56 is connected to the control circuit 46 so as to be operated under control of the control circuit 46.

Also, it is possible to apply an electrical locking to the device so as to inhibit the inhaling action of the user in addition to the lighting of the lamp 56 in order to inform the user that the remaining amount of the liquid flavor source 34 is small. Incidentally, it is also possible to use as the sensor 54 a non-contact type sensor which detects a change in the remaining amount of the liquid flavor source 34 as a change in the reflectance of, for example, an ultrasonic wave.

A pouring port 58 for replenishing the liquid flavor source 34 is connected to the liquid container 32. An end portion of the pouring port 58 is exposed to the outside of the casing 12 so as to permit pouring the liquid flavor source 34 into the liquid container 32. Usually, a removable cap 59 is provided in the exposed end portion of the pouring port 58. As described previously, the liquid container 32 has an inner volume large enough to store the liquid flavor source 34 in an amount corresponding to a plurality of puffs of the flavor enjoyed by the user. However, since the liquid flavor source 34 can be replenished, the flavor-generating device of the present invention can be used continuously without replacing or exchanging the liquid container 32.

Incidentally, a transparent peeping window (not shown) can be formed in that portion of the side wall of the casing 12 which corresponds to the liquid container 32 in place of using the liquid amount sensor 54 in order to observe the remaining amount of the liquid flavor source 34 within the liquid container 32. In this case, the liquid container 32 itself must be formed of a transparent or translucent material. Naturally, the remaining amount of the liquid flavor source 34 within the liquid container 32 can be observed through the peeping window so as to find the timing of replenishing the liquid flavor source 34. It is also possible to employ an optical system using a prism for observing the remaining amount of the liquid flavor source 34 within the liquid container 32.

The flavor-generating device 10 shown in FIG. 1 can operated as in the following manner, in which the heater switch 48 is kept turned off.

Specifically, where the device 10 is used for inhaling a flavor, the power source switch 50 is turned on first by a user. Then, the mouth piece 16 is taken in the mouth of the user for the inhaling action through the inhalation port 22. As a result, an inhaling action signal is transferred from the sensor 52 to the control circuit 46. Then, under the control of the control circuit 46, an electric power is supplied from the power source 44 to the heater 42 so as to turn the heater 42 on.

In this step, the liquid flavor source 34 is already transported to the outlet port 36a of the capillary tube 36 by the capillary force of the capillary tube 36 as shown in FIG. 2A. If the heater 42 is turned on under this condition, the liquid flavor source 34 within the outlet port 36a is instantly gasified by the heat generated from the heater 42 as shown in FIG. 2B so as to be supplied into the gas passageway 20. Upon gasification of the liquid flavor source 34 within the outlet port 36a by the heating with the heater 42, the liquid flavor source 34 is newly supplied from the liquid container 32 into the outlet port 36a of the capillary tube 36 by the capillary force of the capillary tube 36, as shown in FIG. 2C. In this fashion, supply and gasification of the liquid flavor source 34 are repeated within the outlet port 36a of the capillary tube 36.

The gasified flavor source is mixed with the main air introduced through the air intake port 18 and the squeeze hole 24a into a region around the outlet port 36a of the capillary tube 36 in accordance with the inhaling action of the user and, then, the mixture is transferred into the inhalation port 22. The amount of the air introduced through the outer air inlet port 26 can be changed during the inhaling action, if necessary, by controlling the adjusting shutter 28. It follows that the taste of the air containing a flavor, which is transferred to the inhalation port 22, can be changed appropriately in accordance with the preference of the user.

Figure 3:
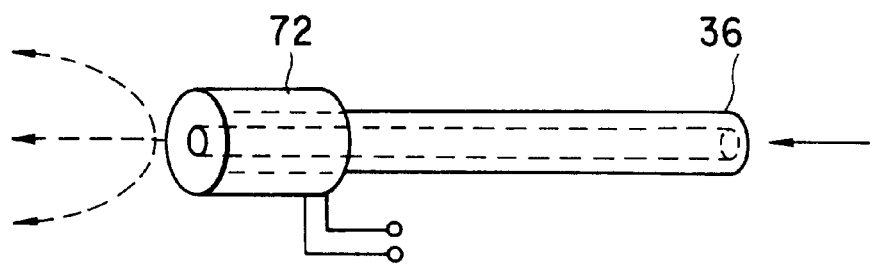
FIG. 3 is a perspective view showing a modification of the mechanism for supplying and gasifying a liquid flavor source according to the invention.
Figure 4:
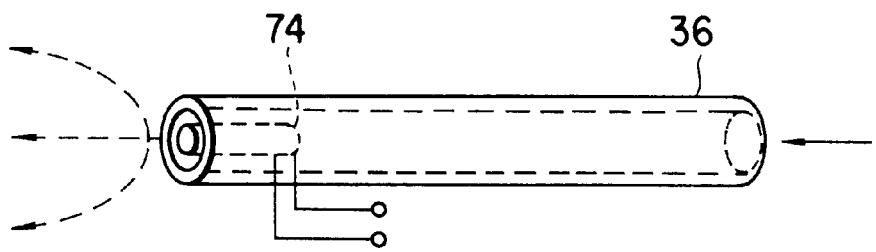
FIG. 4 is a perspective view showing another modification of the mechanism for supplying and gasifying a liquid flavor source.
Figure 5:
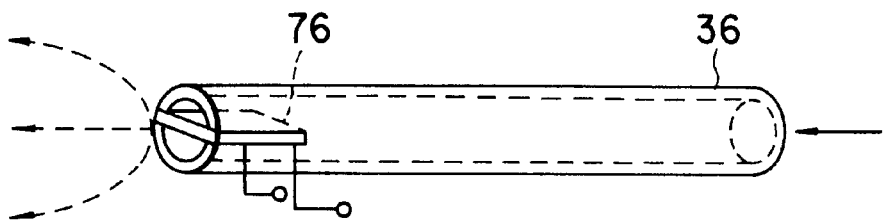
FIG. 5 is a perspective view showing still another modification of the mechanism for supplying and gasifying a liquid flavor source according to the invention.

FIGS. 3 to 5 are perspective views each showing a modification of the mechanism for supplying and gasifying the liquid flavor source 34.

In the modification shown in FIG. 3, a ring-shaped heater 72 is arranged to cover the outlet port 36a of the capillary tube 36.

In the modification shown in FIG. 4, a rod-like heater 74 is inserted into the outlet port 36a of the capillary tube 36.

Further, in the modification shown in FIG. 5, a plate-like heater 76 is inserted into the outlet port 36a of the capillary tube 36.

Any of these modifications permits producing the particular function described previously in conjunction with the embodiment shown in FIG. 1.

Figure 6:
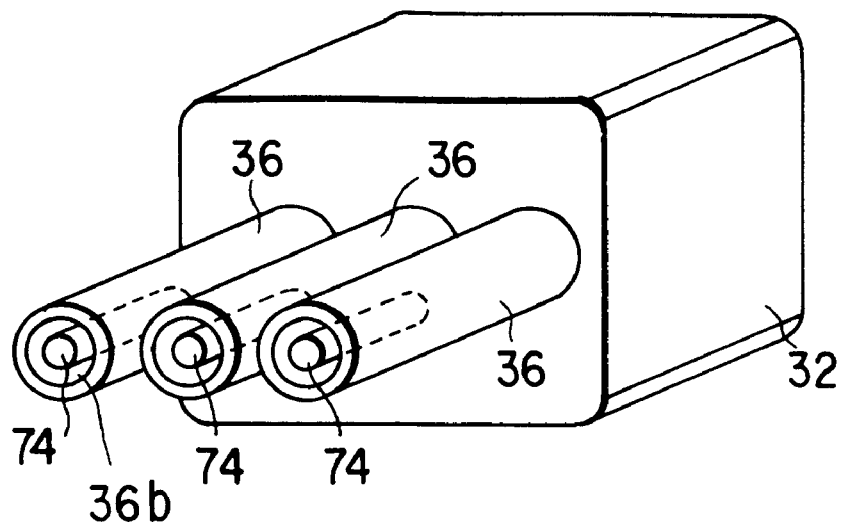
FIG. 6 is a perspective view showing still another modification of the mechanism for supplying and gasifying a liquid flavor source according to the invention.
Figure 7:
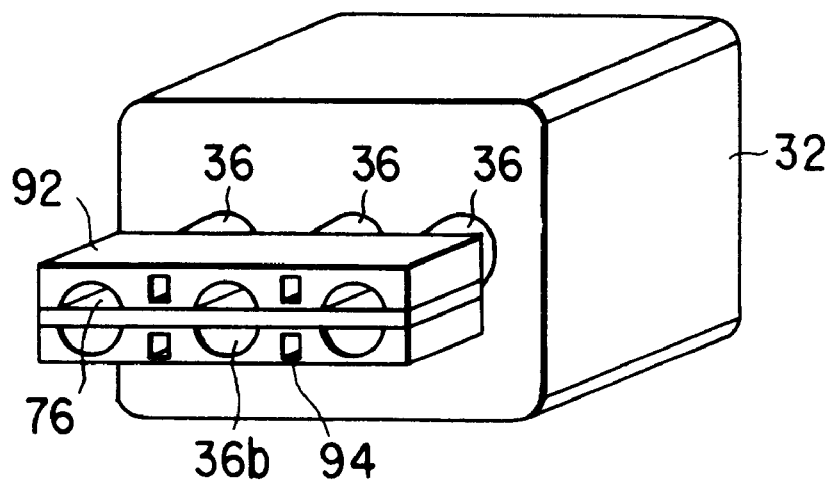
FIG. 7 is a perspective view showing still another modification of the mechanism for supplying and gasifying a liquid flavor source according to the invention.

FIGS. 6 and 7 are oblique views each showing an additional modification of the mechanism for supplying and gasifying the liquid flavor source 34.

In the modification shown in FIG. 6, three capillary tubes 36 are inserted into the liquid container 32. In addition, a rod-like heater 74 as shown in FIG. 5 is inserted into the outlet port 36a of each of the capillary tubes 36.

In the modification shown in FIG. 7, three capillary tubes 36 are inserted into the liquid container 32. In addition, a heater frame 92 is mounted to the outlet ports 36a of these three capillary tubes 36. To be more specific, the heater frame 92 is provided with three plate-like heaters 76 as shown in FIG. 6 in a manner to correspond to the three outlet ports 36a of the capillary tubes 36. Further, air passageways 94 are formed between adjacent capillary tubes 36 arranged in the heater frame 94 in a manner to extend in the longitudinal direction of the capillary tube. Of course, the particular construction permits sufficiently mixing the gaseous flavor substance with the air.

Figure 8:
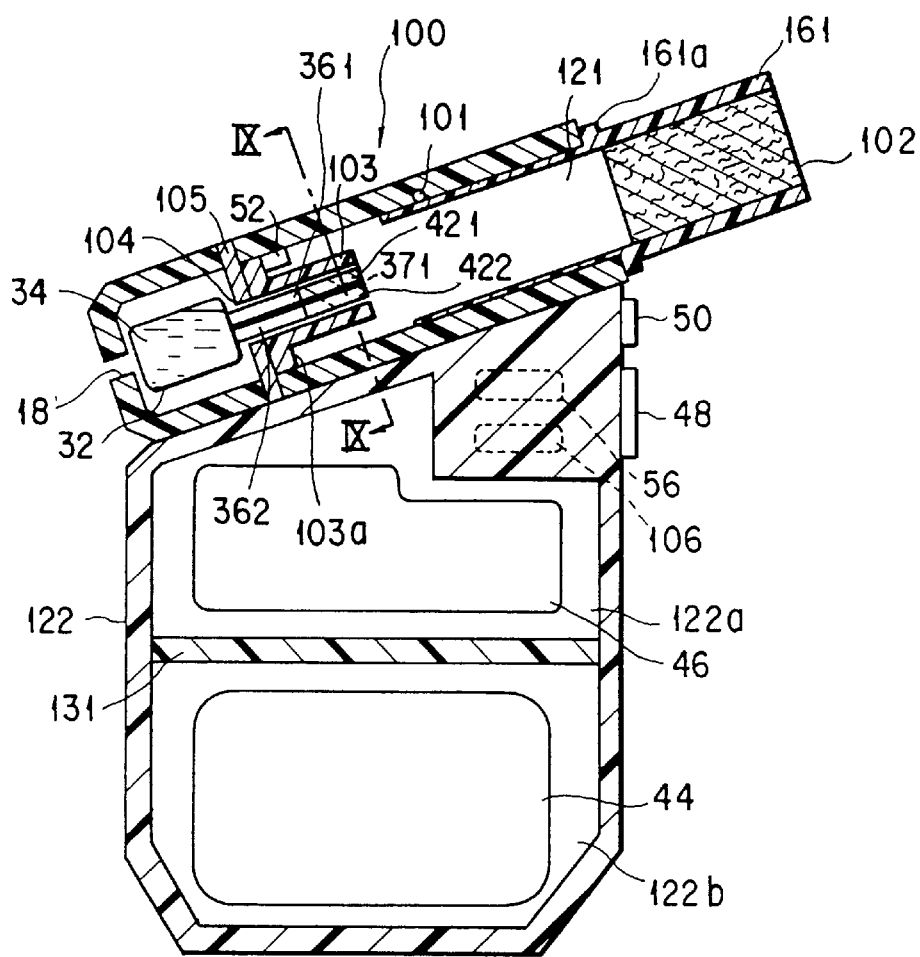
FIG. 8 schematically shows a flavor-generating device according to another embodiment of the present invention.
Figure 9:
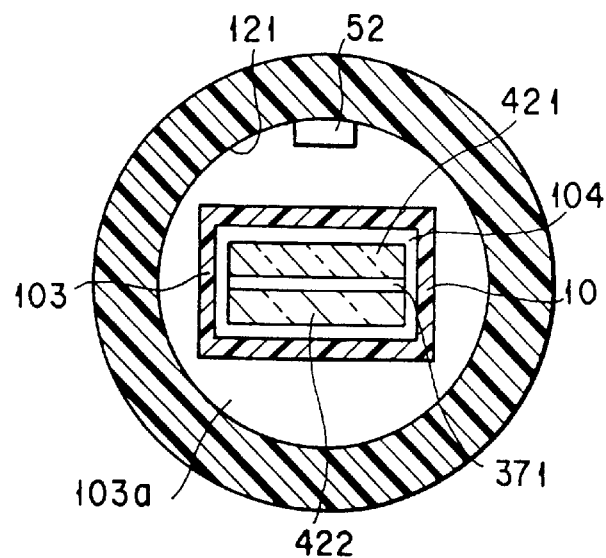
FIG. 9 is a cross-sectional view taken along the line IX—IX of FIG. 8.
Figure 10:
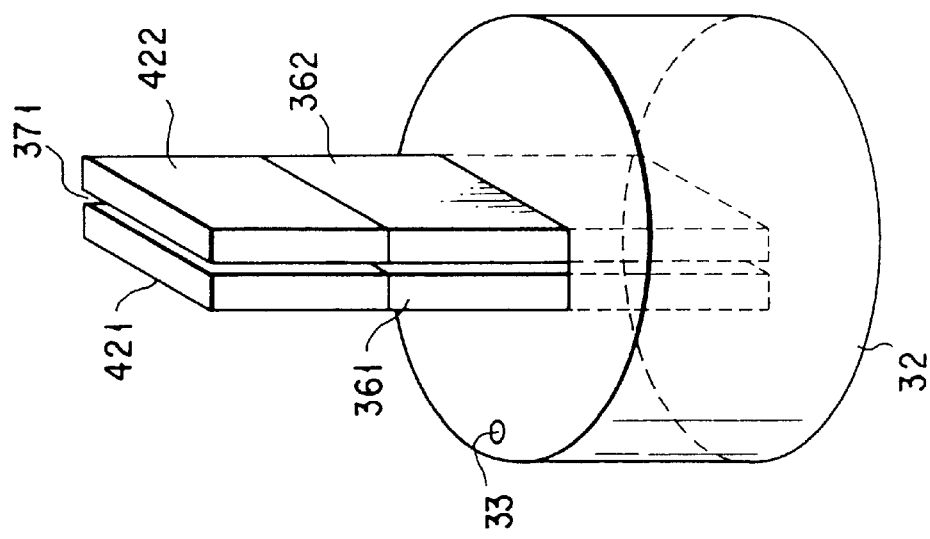
FIG. 10 is a perspective view showing the mechanism for supplying and gasifying a liquid flavor source used in the flavor-generating device of FIG. 8.

FIG. 8 schematically shows the construction of a flavor-generating device according to another embodiment of the present invention. FIG. 9 is an enlarged cross-sectional view taken along the line IX—IX of FIG. 8. FIG. 10 is a perspective view showing the liquid passageway and the heater together with the liquid container used in the device of FIG. 8. The same or similar members of the device as in FIG. 1 are denoted by the same reference numerals and the detailed explanation thereof is omitted in the following description.

In the device 100 shown in FIG. 8, the upper chamber 121 and the lower chamber 122 constitutes separate chamber unlike the device shown in FIG. 1 wherein one casing is partitioned by the partition wall 13 into the two chambers. The lower chamber 122 has an inclined upper wall. The upper chamber 121, which has a hollow cylindrical shape closed at one end (lower end), is provided on the lower chamber 121 along the inclined upper wall of the lower chamber 122. Thus, the upper chamber 121 is correspondingly inclined as a whole. The lower chamber 122 is partitioned by a partition wall 131 into an upper sub-chamber 122a, which houses the control circuit 46, and a lower sub-chamber 122b, which houses the electric power source 14. In the device shown in FIG. 8, the electrical connections are essentially the same as those in the device shown in FIG. 1, and thus are not shown in FIG. 8.

The air intake port 18 like one shown in FIG. 1 is provided at the closed end (lower end) of the upper chamber 121. A mouthpiece 161 may be detachably inserted directly, i.e., without through a holder, into the open end portion (upper end portion) of the upper chamber 121. The mouthpiece 161 has on its periphery a protrusion 161a for engaging with the open end edge so as to prevent a further insertion thereof into the upper chamber 121. A mouthpiece sensor 101 is provided on the upper wall of the upper chamber 121 for detecting the sufficient insertion of the mouthpiece 161. Such a position sensor 101 is known per se. Further, a filter 102 may be inserted into the mouthpiece 161 over the region from the position corresponding to the protrusion 161a to the proximal end of the mouthpiece 161, i.e. inhalation portion of the mouthpiece 161, as shown in FIG. 8.

Further, a small exchangeable liquid container 3:2 containing the liquid flavor source and having an opening (not shown) like the opening 33 in FIG. 1 is arranged in the upper chamber 121 so as not to clog the air intake port 18. A liquid passageway 371 for the liquid flavor source is provided in fluid communication with the liquid flavor source 34 in the container 32. In the device shown in FIG. 8, the liquid passageway 371 is defined between two substantially parallel plates spaced apart from each other. The distal end portion (the outlet portion of the liquid flavor source) of the liquid passageway 371 is heated by plate-like heaters 421 and 422 mounted to the plate 361 and 362, respectively.

More specifically, as shown in FIG. 10, the two plates 361 and 362 are arranged in substantially parallel, and space apart from each other with a distance sufficient for the capillary force to be exerted therebetween. The distance is preferably 0.01 mm to 2.0 mm. In the embodiment shown in FIG. 10, the plate heaters 421 and 422 have the same thickness as the plates 361 and 362, respectively, and are spaced apart with the same distance as in the plates 361 and 362. Thus, in this case, the outlet portion of the liquid passageway 371 is constituted by the heaters 421 and 422.

It should be noted in the present invention that the liquid passageway defined by the substantially parallel plates is fluid-tightly sealed at its sides by a sealing material (not shown) such as a plastic film or a metal foil so as to prevent the leakage or the evaporation of the liquid flavor source from the sides of the plates.

Returning to FIG. 8, that portions of the plates including the heaters which protrude from the container 32 are surrounded by a cylindrical body 103 spaced apart from the plates with a predetermined distance. The cylindrical body 103 has a flange at its lower end portion. The flange 103a engages with the inner peripheral wall of the upper chamber 121. As shown in FIG. 9, the cylindrical body may have a rectangular cross section, and defines an air passageway 104 between it and the plates. The air passageway (air guiding path) 104 guides, along it, the air introduced by the inhalation action of the user from the air intake port 18 provided at the closed end edge of the upper chamber 121. The introduced air embraces or surrounds the gasified liquid flavor source at the outlet portion of the liquid passageway 371, and is directed toward the inhalation port by the air passageway 104. Thus, the gasified flavor source does not tend to be condensed or deposited on the inner wall of the upper chamber 121, and if any, the gasified flavor source is condensed or deposited on the inner wall of mouthpiece 161. Therefore, the deposited flavor source can be removed from the device by cleaning or exchanging the mouthpiece. Further, by providing the air guiding path 104 which can direct the air locally or selectively to the gasified flavor source at the outlet portion of the liquid passageway, an aerosol formation efficiency can be more enhanced when the liquid flavor source contains the aerosol generation material, since the mixing of the gasified flavor source with the air and the cooling of the gasified flavor source thereby can be simultaneously effected efficiently by means of the air stream passing through the air guiding path 104.

Incidentally, it is possible to provide an air flow rate-adjusting dial 105, which is known per se, arranged downstream of the cylindrical body 103 and upstream of the liquid container 32. By means of the air flow rate-adjusting dial 105, the user can set the air flow rate and hence the suction resistance in accordance with the user's preference. Further, a display mechanism 106 for indicating the remaining amount of the power source 44 connected to the control circuit may be provided as shown in FIG. 8.

Figure 11:
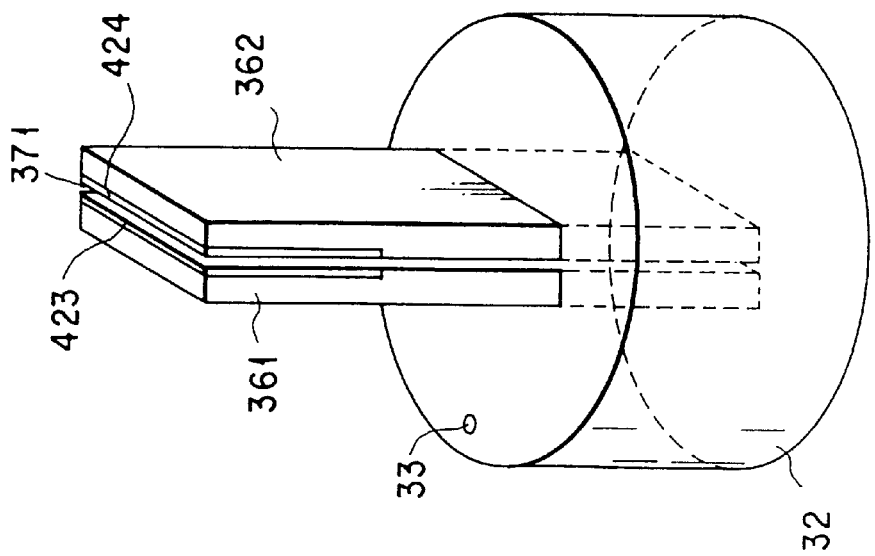
FIG. 11 is a perspective view showing still another modification of the mechanism for supplying and gasifying a flavor source.

FIG. 11 is a perspective view illustrating a modification of the mechanism for supplying and gasifying the liquid flavor source shown in FIG. 10. In FIG. 11, plate heaters 423 and 424 are provided in the opposing surface regions of the plates 361 and 362 defining the liquid passageway therebetween.

Figure 12:
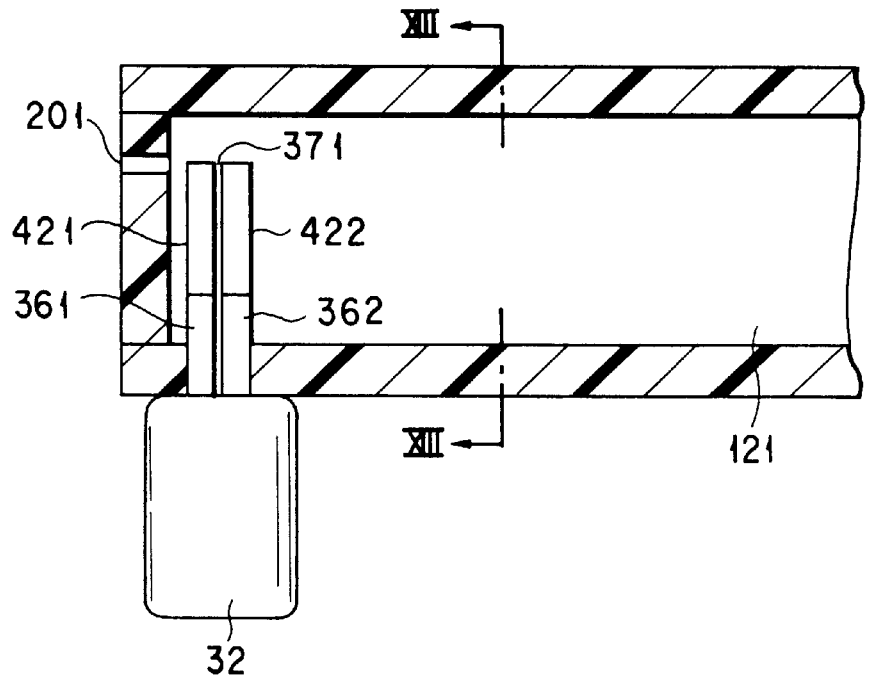
FIG. 12 is a perspective view showing still another modification of the mechanism for supplying and gasifying a liquid flavor source according to the invention.
Figure 13:
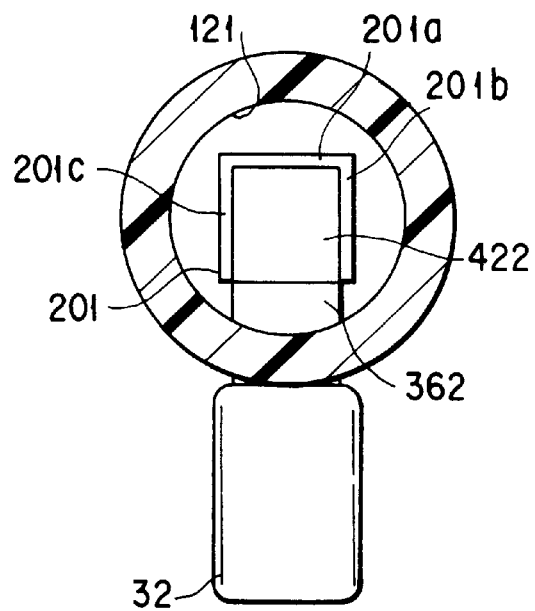
FIG. 13 is cross-sectional view taken along the line XII—XII of FIG. 12.

FIG. 12 is a perspective view showing still another modification of the mechanism for supplying and gasifying a liquid flavor source used in the device according to the invention. FIG. 13 is a cross-sectional view taken along the line XIII—XIII of FIG. 12. In the mechanism shown in FIG. 12, the two plates 361 and 362 and the two plate heaters 421 and 422, like the ones shown in FIG. 10, which define the liquid passageway 371 in fluid communication with the liquid flavor source in the container 32 penetrate the peripheral wall of the upper chamber 121 from below the upper chamber into the inside the upper chamber 121. One end of the upper chamber 121 is closed, and an air passageway 201 which communicates with the outer atmospheric air outside the upper chamber 121. As shown in FIG. 13, the air passageway 201 is formed along the outer contour of the heaters 421 and 422, and consists of a laterally elongated upper passageway portion 201a having a length slightly larger than the width of the plates 361 and 362, side passageway portions 201b and 201c which are connected to the upper portion 201a at its both end and extend to the positions corresponding to the lower ends of the heaters 421 and 422. The passageway 201 can produce the same or similar effects noted above as those which the air passageway 104 shown in FIG. 9 or 8 produces.

Figure 14:
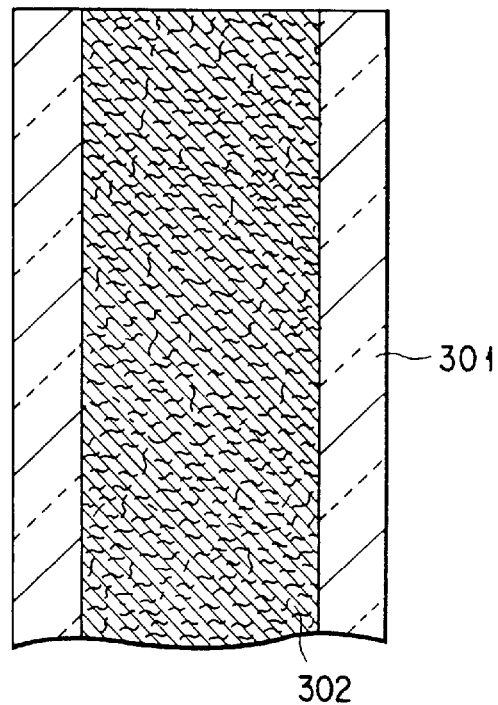
FIG. 14 is a cross-sectional view showing another embodiment of the liquid passageway for a liquid flavor source used in a flavor-generating device according to the invention.
Figure 15:
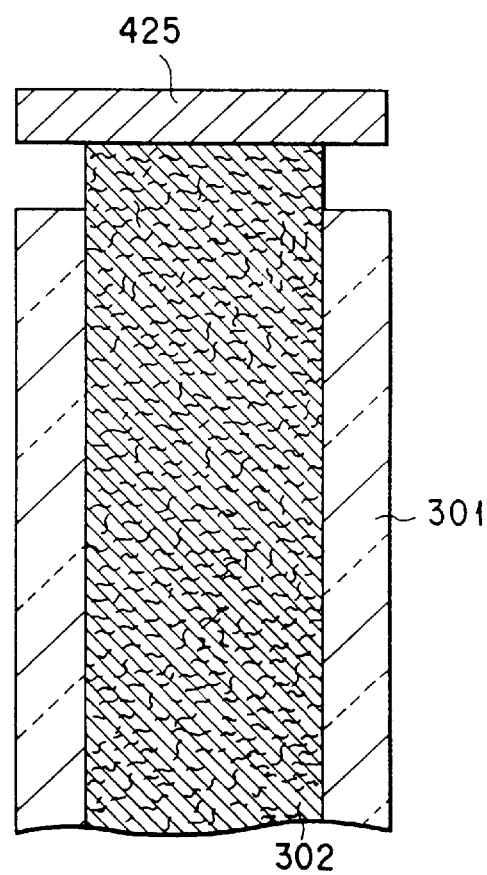
FIG. 15 is a cross-sectional view showing still another embodiment of the liquid passageway for a liquid flavor source used in a flavor-generating device according to the invention.

FIG. 14 is a cross-sectional view showing another embodiment of the liquid passageway for a liquid flavor source used in a flavor-generating device according to the invention. In this case, a liquid passageway 372 is constituted by the intercommunicating pore structure 302 filled in an enclosure 301, as mentioned earlier. The enclosure 301 may be provided by a tube, or two plates arranged spaced apart from each other wherein the both sides are sealed. In this embodiment, a heater or heaters (not shown) may be arranged as in FIG. 1, 10 or 11. Further, as shown in FIG. 15, the intercommunicating pore structure 302 may protrude from the enclosure 301. In such a case, a heater 425 can be provided on the protruded end of the intercommunicating pore structure 302.

FIG. 15 is a cross-sectional view showing still another embodiment of the liquid passageway for a liquid flavor source used in a flavor-generating device according to the invention.

In order to facilitate the understanding of the present invention, the features of the present invention are described with reference to some embodiments and modifications of the present invention. However, these features can be combined appropriately depending on the object of the flavor-generating device. In other words, the present invention can be worked in various modes other than the embodiments shown in the drawing within the technical scope of the present invention.

As described above, the present invention provides a flavor-generating device, which can be driven with a low energy, which permits preventing the liquid flavor source from being wasted, and which permits generating a flavor substance when a user takes a puff of the flavor substance.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flavor-generating device comprising:
a chamber having an air inlet port for introducing the air thereinto and an inhalation port through which a user inhales a flavor, and defining a gas passageway between the air inlet port and the inhalation port;
a liquid container for storing a liquid containing a flavor substance, and maintained at substantially an atmospheric pressure;
at least one liquid passageway having a first end portion which is in a fluid communication with the liquid and a second end portion which is in a fluid communication with the gas passageway, for transporting the liquid from the liquid container to the second end portion by capillary force, the capillary force being created predominantly by the attraction between the liquid containing a flavor substance and an interior of the liquid passageway; and
a heater mounted at the second end portion of the at least one liquid passageway, for heating and gasifying the liquid transported from the liquid container, the heater heating and gasifying said liquid while it is disposed in said second end portion, thereby forming a gaseous stream of said liquid exiting said second end portion into said chamber for inhalation through said inhalation port.

2. The device according to claim 1, wherein said at least one liquid passageway includes at least one capillary tube.

3. The device according to claim 1, wherein said at least one liquid passageway includes at least one pair of substantially planar elements spaced apart from each other.

4. The device according to claim 1, wherein said at least one liquid passageway includes an intercommunicating pore structure filled in an enclosure.

5. The device according to claim 1, wherein said heater is mounted at the tip end of the at least one liquid passageway.

6. The device according to claim 1, wherein said at least one liquid passageway includes a plurality of liquid passageways, each passageway including a capillary tube equipped with a heater.

7. The device according to claim 1, further comprising detecting means for detecting the inhaling action of a user; and control means for controlling the heater such that said heater is driven upon inhaling action of the user.

8. The device according to claim 1, wherein said air passageway is formed to permit the air to be introduced selectively toward the second end portion of the at least one liquid passageway.

9. The device according to claim 1, wherein said liquid container is exchangeably mounted.

10. The device according to claim 2, wherein said at least one capillary tube has a diameter of between about 0.01 mm and 3 mm.

11. The device according to claim 10, wherein said at least one capillary tube has a diameter of between about 0.05 mm and 1 mm.

12. The device according to claim 2, wherein said liquid container has an opening for access by said at least one capillary tube into said container, and an opening exposed to ambient atmospheric pressure, the opening to ambient atmospheric pressure allowing atmospheric pressure to be maintained within said container.

13. The device according to claim 2, wherein said heater includes an annular element disposed at the second end portion of each at least one capillary tube.

14. The device according to claim 2, wherein said heater is a cylindrical element.

15. The device according to claim 2, wherein said heater includes at least one planar element, one planar element extending across a diameter of each said at least one capillary tube.

16. The device according to claim 6, further comprising a heater frame partially surrounding the second end portion of each of said plurality of capillary tubes.

17. The device according to claim 3, wherein the space between each said pair of substantially planar elements is partially closed by a film placed on sides of the planar elements, with the second end of the at least one liquid passageway remaining open.

18. The device according to claim 3, wherein the heater includes heating elements provided on opposed faces of each said at least one pair of substantially planar elements.

* * * * *